US00PP24346P3

(12) United States Plant Patent
Schoone

(10) Patent No.: US PP24,346 P3
(45) Date of Patent: Mar. 25, 2014

(54) ***PHALAENOPSIS* ORCHID PLANT NAMED 'DAME BLANCHE'**

(50) Latin Name: ***Phalaenopsis* hybrid**
Varietal Denomination: Dame Blanche

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/506,412

(22) Filed: Apr. 18, 2012

(65) Prior Publication Data

US 2012/0272419 P1 Oct. 25, 2012

Related U.S. Application Data

(60) Provisional application No. 61/478,785, filed on Apr. 25, 2011.

(30) Foreign Application Priority Data

Apr. 27, 2011 (NL) ..... OPS788

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Dame Blanche' particularly characterized by flowers which are white; on the lateral sepals a haze of green/yellow and red/purple; the labellum is white with yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Dame Blanche'.

CROSS-REFERENCE TO RELATED APPLICATIONS

This application claims priority to U.S. Provisional Application No. 61/478,785, filed Apr. 25, 2011 and Netherlands Plant Breeders' Rights Application No. OPS788, filed Apr. 27, 2011. The disclosure of both prior applications are hereby incorporated by reference in their entirety.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Dame Blanche'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Dame Blanche' is a product of a controlled breeding program conducted by the inventor, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Dame Blanche' originated from a cross made by the inventor in 1998 in Strengweg, Heemskerk, The Netherlands. The female or seed parent is the *Phalaenopsis* cultivar designated '(Winter Kaala×amabilis)', unpatented. The male or pollen parent is the *Phalaenopsis* cultivar designated 'Spring Song', unpatented. The new *Phalaenopsis* 'Dame Blanche' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in November, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Dame Blanche', which in combination distinguish this *Phalaenopsis* as a new and distinct cultivar:

1. flowers which are white; on the lateral sepals a haze of green/yellow and red/purple; The labellum is white with yellow and purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Dame Blanche', the female parent '(Winter Kaala×amabilis)' has white flowers and they are about 10 cm high, the male parent 'Spring Song' has white colored flowers and they are about 12 cm high, whereas the flowers of 'Dame Blanche' are white and are about 11 cm high.

Presently, there is no commercial cultivar to which 'Dame Blanche' can be meaningfully compared.

BRIEF DESCRIPTION OF THE PHOTOGRAPHS

The accompanying photographs illustrate the overall appearance of the new *Phalaenopsis* 'Dame Blanche' showing the colors as true as is reasonably possible with colored reproductions of this type. Colors in the photographs may differ slightly from the color values cited in the detailed botanical description, which accurately describe the color of 'Dame Blanche'.

DETAILED BOTANICAL DESCRIPTION

Figure 1:
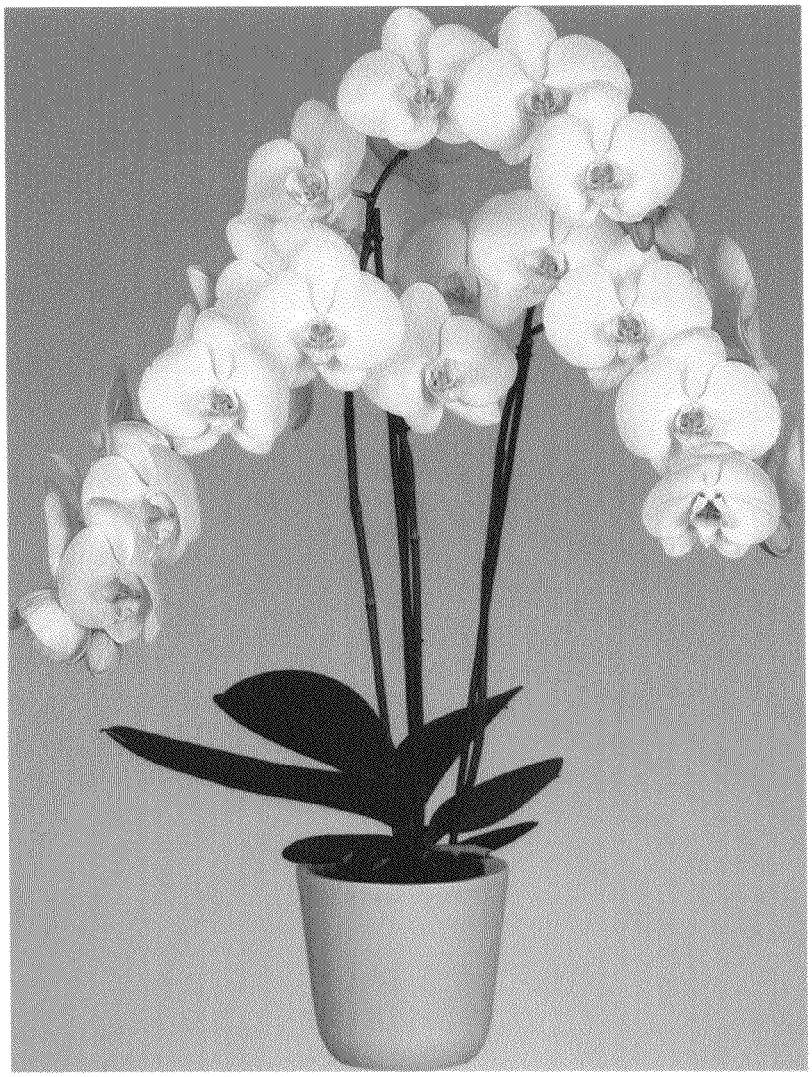
FIG. 1 shows a side view perspective of a typical flowering plant of 'Dame Blanche' in a 12 cm pot, at 16 months of age.

The new *Phalaenopsis* cultivar 'Dame Blanche' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Dame Blanche' as grown in a greenhouse in Strengweg, Heemskerk, The Netherlands, under conditions which closely approximate those generally used in commercial practice. Initially, the ideal temperature to grow plants of 'Dame Blanche' is 27° C. during the day and at night. Then, during the flowering phase of 'Dame Blanche', the ideal growing temperature is 20-22° C. during the day and 18° C. at night. Light levels for growing 'Dame Blanche' are a minimum of 5,000 lux and a maximum of 10,000 lux. A balanced fertilizer with level of 200 ppm N, 87 ppm P, 168 ppm K is applied. Duration of growth of 'Dame Blanche' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Dame Blanche' plants described is 12 months after potting.

Classification:

*Botanical.*—*Phalaenopsis* hybrid.

Parentage:

*Female or seed parent.*—*Phalaenopsis* cultivar designated '(Winter Kaala×amabilis)', unpatented.

*Male or pollen parent.*—*Phalaenopsis* cultivar designated 'Spring Song', unpatented.

Propagation:

*Type.*—Tissue culture.

*Rooting habit and description.*—Approximately 5 mm-6 mm wide and greyed/green (RHS 190C and RHS 195A) in color; freely branching. It takes 12 weeks for plants growing in tissue culture to initiate roots.

Plant:

*Size at maturity.*—Height: about 61 cm. Spread: about 40 cm to 50 cm.

*Growth habit.*—Standard; green (RHS 137A) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 19 to 24 cm.

*Mature leaf width.*—About 7 and 9 cm.

*Mature leaf thickness.*—About 2 mm.

*Mature leaf color.*—Upper side: green RHS 137A. Under side: yellow-green RHS 146B.

*Leaf base.*—Acute.

*Margin.*—Entire.

*Venation.*—Pattern: parallel. Color of midvein: upper side: green RHS 137A. Under side: yellow-green RHS 146B.

Raceme:

*Quantity per plant.*—About 1 to 2.

*Number of flowers per raceme.*—About 5 to 10.

*Length.*—About 55 and 65 cm.

*Diameter.*—About 5 mm.

*Strength.*—Strong.

*Aspect.*—Upright.

*Texture.*—Glabrous and smooth.

*Color.*—Brown (RHS N200A) with yellow-green spots (RHS 144C).

*Internode.*—Length: about 30 to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 mm to 30 mm. Diameter (at midpoint): about 15 mm to 25 mm. Shape: egg-shaped. Color: yellow-green (RHS 145A) with some purple (RHS N79C).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
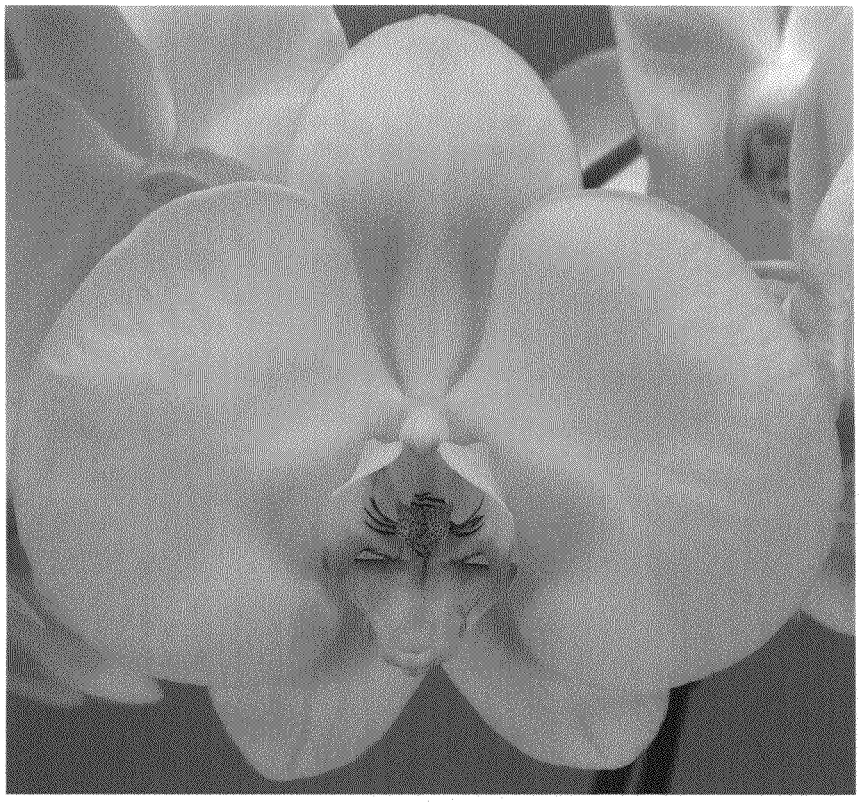
FIG. 2 shows a close-up view of the typical buds and flowers of 'Dame Blanche'.
Figure 3:
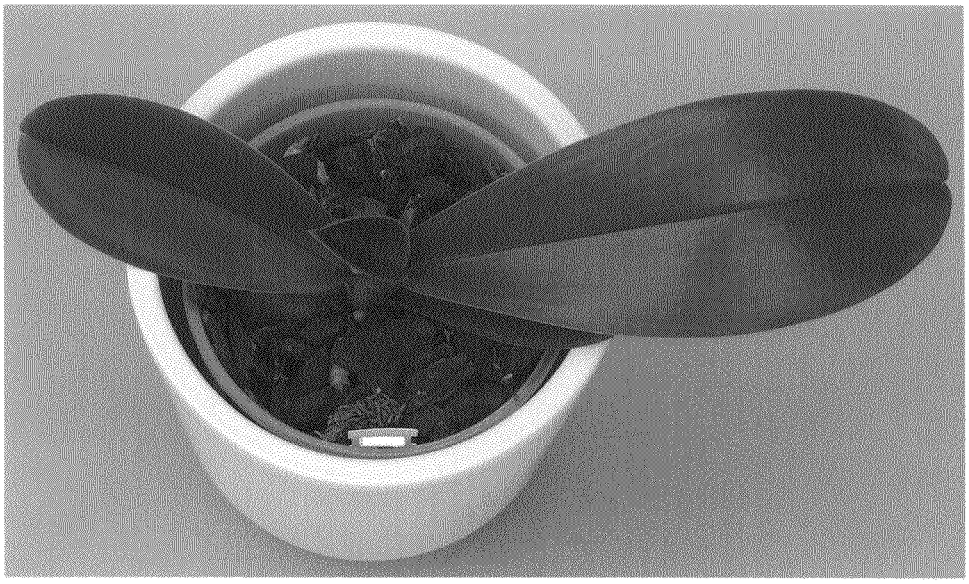
FIG. 3 shows a close-up view of the typical leaves of 'Dame Blanche'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 95 mm. Diameter: about 105 mm. Depth of tube: about 15 mm.

*Petals.*—Quantity and arrangement: six petals and sepals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 62 mm. Width: about 45 mm. Texture: Upper surface: smooth and satiny. Under surface: smooth and satiny. Color (when fully opened): upper surface: white (RHS NN155C). Under surface: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: ovate. Length: about 28 mm. Width (not flattened): about 25 mm. Texture: Upper and under surface: smooth and satiny. Color (when fully opened): Upper surface: the main color of the midlobe and the lateral lobes is white (RHS NN155C). The midlobe has also some red-purple (RHS 71A) and yellow (RHS 2B). In the center of the lateral lobes are red-purple stripes (RHS 71A) and the bottom edge is yellow (RHS 2B). Under surface: midlobe: main color is white (RHS NN155C). Corners are yellow (RHS 2A) and at the base some red-purple (RHS 71A). Lateral lobes: main color is white (RHS NN155C). Bottom edges are yellow (RHS 2A). At the base also some red-purple (RHS 71A). Chirri: color: yellow (2B). Pestle (Callosities): Length: about 4 mm. Width (not flattened): about 5 mm. Color: yellow (RHS 3A) with red/purple stripes and spots (RHS 71A).

*Sepals.*—Arrangement: Outer whorl comprises 3 sepals. Overall shape: elliptical and weakly cupped. Margin: entire and weakly undulate. Length: about 50 mm. Width: about 30 mm to 40 mm. Apex: oval/round. Texture: Upper and under surface: smooth and satiny. Color (when fully opened): Upper surface: white (RHS NN155C). On the lateral sepals there is a haze of green-yellow (RHS 1C) and red-purple (RHS 64B). Under surface: white (RHS NN155C) with yellow-green in the center (RHS 154C) and red-purple (RHS 64B). Pedicel: Length: about 45 mm. Diameter: about 3 to 4 mm. Texture: glabrous and smooth. Color: yellow-green (RHS 145C) with RHS 146C.

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 11 mm. Diameter: about 7 mm. Color: white (RHS NN155C).

*Pollinia.*—Quantity: Two. Diameter: about 1 mm. Color: orange (RHS N25A).

*Ovary.*—Length: about 5 mm. Diameter: about 5 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Dame Blanche', as illustrated and described herein.

* * * * *